(12) United States Patent
Suzuki et al.

(10) Patent No.: US 6,451,187 B1
(45) Date of Patent: Sep. 17, 2002

(54) AIR/FUEL RATIO SENSOR

(75) Inventors: Seikou Suzuki, Hitachiohta; Masahiro Komachiya, Hitachi; Tsuyoshi Fujita, Yokohama, all of (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/467,379

(22) Filed: Dec. 21, 1999

(30) Foreign Application Priority Data

Dec. 21, 1998 (JP) ............................................. 10-362475

(51) Int. Cl.[7] ............................................. G01N 27/407
(52) U.S. Cl. ........................ 204/426; 204/408; 204/425; 204/429; 205/781; 205/784.5; 205/785; 422/98
(58) Field of Search .................. 204/408, 421–429; 422/98

(56) References Cited

U.S. PATENT DOCUMENTS

| | | | |
|---|---|---|---|
| 4,304,652 A | * | 12/1981 | Chiba et al. |
| 4,457,161 A | * | 7/1984 | Iwanaga et al. |
| 4,464,244 A | * | 8/1984 | Uchida et al. |
| 4,487,680 A | * | 12/1984 | Logothetis et al. |
| 4,861,456 A | * | 8/1989 | Mase et al. |
| 5,186,809 A | * | 2/1993 | Aoyama et al. |
| 5,242,573 A | * | 9/1993 | Hayakawa et al. |
| 5,460,711 A | * | 10/1995 | Riegel et al. |
| 5,624,640 A | * | 4/1997 | Potthast et al. |
| 5,935,399 A | * | 8/1999 | Tanaka et al. |
| 6,007,688 A | * | 12/1999 | Kojima et al. |
| 6,238,536 B1 | * | 5/2001 | Lundgren et al. |
| 6,241,865 B1 | * | 6/2001 | Cappa et al. |

OTHER PUBLICATIONS

Seikoo Suzuki et al., Thick–Film Zirconia Air–Fuel Ratio Sensor with a Heater for Lean Mixture Control Systems, 850379, SAE Technical Paper Series, pp. 62–67, 1985. Month unavailable.

* cited by examiner

Primary Examiner—T. Tung
(74) Attorney, Agent, or Firm—Crowell & Moring, LLP

(57) ABSTRACT

A detector for an air/fuel ratio sensor, which is comprised of a structure formed by stacking an oxygen reference electrode, a dense zirconia solid electrolyte, a negative electrode, a porous zirconia solid electrolyte, a positive electrode and a porous protection film on one another, is formed over a ceramic substrate having a heater built therein. Thus, a combined air/fuel ratio sensor can be obtained which is operated in a short time (about 5 seconds or less) after power-on so as to comply with emission control applied immediately after startup and provides low power consumption and a high degree of reliability.

12 Claims, 13 Drawing Sheets

NOTE: CONCENTRATION OF VERTICAL AXIS IS SHOWN AS SIMPLE GUIDE

CATALYTIC ACTION OF Pt: $O_2 \rightarrow O^{--} \rightarrow O_2$

EXHAUST GAS FLOW

AIR/FUEL RATIO SENSOR

BACKGROUND OF THE INVENTION

The present invention relates to an air/fuel ratio sensor for detecting an air/fuel ratio from the concentration of remaining oxygen in an exhaust gas from a vehicle engine, a combined air/fuel ratio sensor for detecting the concentrations of exhaust gas components in addition to the air/fuel ratio, and an engine combustion control system using these air/fuel ratio sensors.

An air/fuel ratio sensor has heretofore been known which detects rich to lean air/fuel ratios utilizing an oxygen pump phenomenon of a zirconia solid electrolyte having oxygen ion conductivity and diffusion controlled phenomena of various exhaust gas components. This type of air/fuel ratio sensor needs to apply heat (e.g., about 700° C.) to a sensor element by means of a heater to activate a solid electrolyte.

In order to make it possible to operate the sensor in a short time after power-on, there has recently been proposed a technique for bringing a zirconia solid electrolyte, a platinum electrode, a gas diffusion resistance layer (gas diffusion controlled layer), etc., which form an air/fuel ratio detector, into a laminated structure and laminating such a laminated body (air/fuel ratio detector) and a heater in integral form.

For example, one having a combined structure obtained by integrally calcining a zirconia solid electrolyte placed in a green-sheet state together with a ceramic substrate having a heater built therein has been known in SAE Paper 850379 and the like.

There is also known a combined air/fuel ratio sensor or the like wherein an exhaust gas sensor for detecting the concentrations of HC and NOx in exhaust gas components is integrally combined with an air/fuel ratio detector for detecting a ratio between air and a fuel supplied to an engine.

However, one in which the air/fuel ratio detector of the laminated body is integrally formed with the heater in laminated form, has been not yet in the actual use because of insufficient reliability under its use environment. This is because according to the discussions of the present inventors, a crack is produced in the detector so that the air/fuel ratio sensor is brought into an unserviceable state due to the following reasons. The cause of the occurrence of the crack is roughly divided into the following three groups.

(a) Since the air/fuel ratio detector has a hollow chamber such as an air chamber, it is not possible to effectively transfer the generated amount of heat or heating values of the heater to the detector. Thus, a large temperature gradient occurs between the heater and the air/fuel ratio detector, and the heater is heated at a temperature much higher than at the air/fuel ratio detector. As a result, the detector is apt to break due to a thermal stress developed by the large temperature gradient produced in the direction of the thickness of the detector for the air/fuel ratio sensor. Further, since large warpage occurs in the laminated body having the hollow chamber upon calcining, the laminated body itself is manufactured in a structure apt to break.

(b) A ceramic substrate (which is formed as an alumina substrate in most cases) having a heater built therein and a zirconia solid electrolyte are different in thermal expansion coefficient from each other, and hence a large thermal stress occurs in the detector, so that the detector is apt to break.

(c) A pattern for the heater is concentratedly placed only just below the detector, and hence a sudden temperature gradient occurs in the longitudinal direction of the laminated body of the air/fuel ratio sensor. As a result, a large thermal stress occurs in an end of the heater, which is located on the side opposite to the air/fuel ratio detector as viewed in the longitudinal direction of the laminated body, and the laminated body or the like is apt to break due to the thermal stress.

Thus, the air/fuel ratio sensor having the structure wherein the air/fuel ratio detector is directly heated by the heater, cannot overcome the problem on the reliability. Hence it has been not yet in the actual use. Therefore, the detector should inevitably be heated indirectly by an indirectly heated heater (corresponding to a heater having a structure wherein the heater and detector are separated from each other and a clearance is defined between the two), and a startup time interval (activation time) required to activate the air/fuel ratio sensor was a long time of several tens of seconds. Since the indirectly heated heater is used, power consumption necessary for heating also increases. Since the conventional type air/fuel ratio sensor is long in startup time in particular, this led to a large bottleneck to clear emission control applied immediately after the starting of the engine,

SUMMARY OF THE INVENTION

With the foregoing in view, it is therefore an object of the present invention to provide a high-reliable air/fuel ratio sensor which is operated in a short time (e.g., about 5 seconds or less) after power-on so as to comply with emission control immediately after start-up, and which is capable of measuring lean to rich air/fuel ratio ranges with low power consumption and is excellent in heat resistance and durability (crack control function).

It is another object of the present invention to provide an extremely high-implementable and reliable combined air/fuel ratio sensor capable of allowing the air/fuel ratio sensor to combine with the function of detecting exhaust gas components (e.g., HC and NOx) to thereby implement a combined air/fuel ratio and performing exhaust gas component detection in addition to air/fuel ratio detection by making use of oxygen pump action and gas diffusion controlled action in particular.

It is a further object of the present invention to provide a combustion control system suitable for use in an engine, which is capable of easily clearing emission control applied immediately after the start-up of the engine.

In order to achieve the above objects, the present invention is basically constructed as follows:

(a-1) Namely, the present invention is characterized in that an air/fuel ratio detector is formed of a laminated body obtained by stacking an oxygen reference electrode, a dense solid electrolyte, a negative electrode, a porous solid electrolyte, a positive electrode and a porous protection film on one another, and the air/fuel ratio detector and a ceramic substrate having a heater built therein are joined to each other in laminated form.

(a-2) Another invention proposes an air/fuel ratio sensor wherein at least one of an HC detector and an NOx detector each comprised of an oxide semiconductor is provided side by side over a ceramic substrate with a heater built therein by lamination.

(a-3) A further invention proposes a combined air/fuel ratio sensor wherein the above-described air/fuel ratio detector, an NOx detector obtained by stacking a porous oxide, an NOx detecting electrode and a dense solid electrolyte on one another, and a ceramic substrate having a heater built therein are integrally joined to one another so as to be constructed as one laminated structure.

(a-4) A still further invention proposes a combined air/fuel ratio sensor wherein the above-described air/fuel ratio sensor, an HC detector obtained by stacking a porous oxide, an HC detecting electrode and a dense solid electrolyte on one another, and a ceramic substrate having a heater incorporated therein are integrally joined to one another so as to be constructed as a single laminated structure.

(a-5) A still further invention proposes a combined air/fuel ratio sensor wherein the above-described air/fuel ratio detector and a ceramic substrate having a heater built therein are bonded to each other in laminated form, a part of the porous solid electrolyte is hollowed or cut out, a dense solid electrolyte surrounded by insulating materials is formed in the cut-out portion, and an electrode is formed over the upper surface of the dense solid electrolyte, whereby an NOx detector is constructed.

According to the above construction, the present invention can be constructed as a structure in which no hollow chamber is provided in an air/fuel ratio detector. Similarly, the hollow chamber can be deleted even from the HC detector and NOx detector combined with the air/fuel ratio sensor. By doing so, the time required to heat the air/fuel ratio sensor can be advanced or reduced and the air/fuel ratio sensor can be operated in a short time after power-on. Further, a temperature gradient produced in the direction of the thickness of the detector for the air/fuel ratio sensor becomes small, so that a thermal stress developed due to the temperature gradient is reduced. Furthermore, since no hollow chamber exists, a warpage-free laminated body can be obtained.

Even in the case of the laminated structure having no hollow chamber, rich to lean air/fuel ratios can be detected with satisfactory accuracy in the present invention. However, how to detect an air/fuel ratio and exhaust gas components (HC and NOx) will be described in detail by embodiments (see views showing operation principles in FIGS. 5, 14, 16 and 18) to be described later.

(b) In a still further invention as well, insert members (thermal stress buffer layers) each having an intermediate thermal expansion coefficient between a ceramic substrate having a heater built therein and a solid electrolyte (e.g., zirconia solid electrolyte) of an air/fuel ratio detector are placed between the two, whereby a thermal stress developed in a laminated body of an air/fuel ratio sensor can be reduced.

In particular, there is also proposed an air/fuel ratio sensor wherein a laminated body comprised of an electrode constituting an air/fuel ratio detector, an exhaust gas diffusion controlled layer, and a solid electrolyte having oxygen ion conductivity, and a ceramic substrate having a heater built therein are integrally joined to one another with a thermal stress buffer layer interposed therebetween, and the thermal stress buffer layer is comprised of thermal stress buffer layers corresponding to two or more layers which are varied in compounding ratio of a mixed material for the solid electrolyte and the ceramic substrate by the mixed material.

According to the above-described construction, the compounding ratio to the thermal stress buffer layers (ceramic material and mixed material of solid electrolyte and the same material) increases in ceramic material for one layer and increases in solid electrolyte and same material for another layer. Further, the former layer is joined to the ceramic substrate and the latter layer is joined to the solid electrolyte of the air/fuel ratio detector, thereby making it possible to allow each thermal stress buffer layer to approach the air/fuel ratio detector and ceramic substrate. This is effective in preventing cracks.

(c) A still further invention proposes an air/fuel ratio sensor wherein a pattern for the heater is shaped in the form of such a pattern that the air/fuel ratio detector side is dense and gradually becomes coarse as the same faces an end on the opposite side, of the air/fuel ratio detector, as viewed in the longitudinal direction of the laminated body. If done in this way, then a temperature gradient produced in the longitudinal direction of the laminated body of the air/fuel ratio sensor can be also made slow, and hence a thermal stress developed in a heater end directed toward the pad side on the side opposite to the air/fuel ratio detector can be also reduced.

Typical ones of various inventions of the present inventions have been shown in brief. However, the various inventions of the present application and specific configurations of these inventions will be understood from the following description.

BRIEF DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

DESCRIPTION OF THE PREFERRED EMBODIMENTS

Embodied forms of the present invention will hereinafter be described in detail based on embodiments illustrated in the accompanying drawings.

Figure 1:
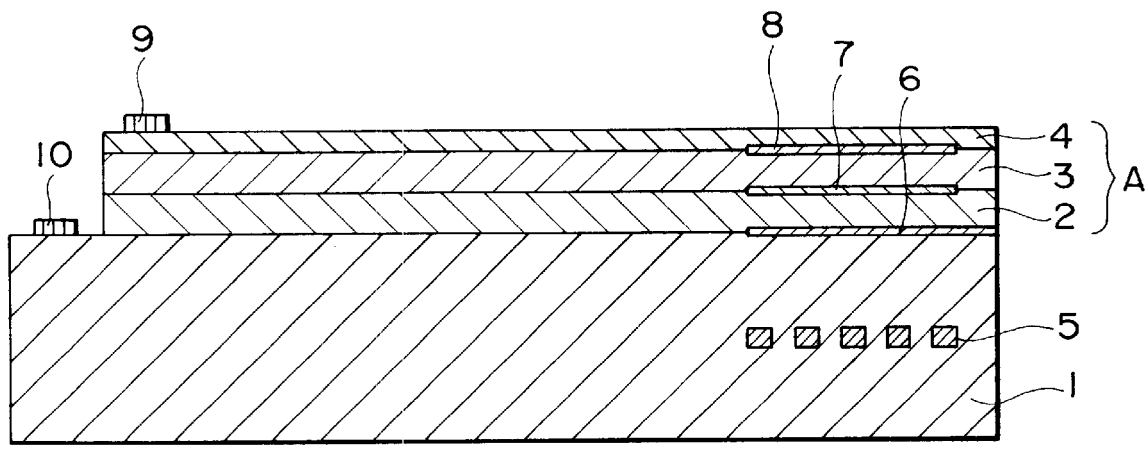
FIG. 1 is a vertical sectional view showing a first embodiment of an air/fuel ratio sensor according to the present invention.
Figure 2:
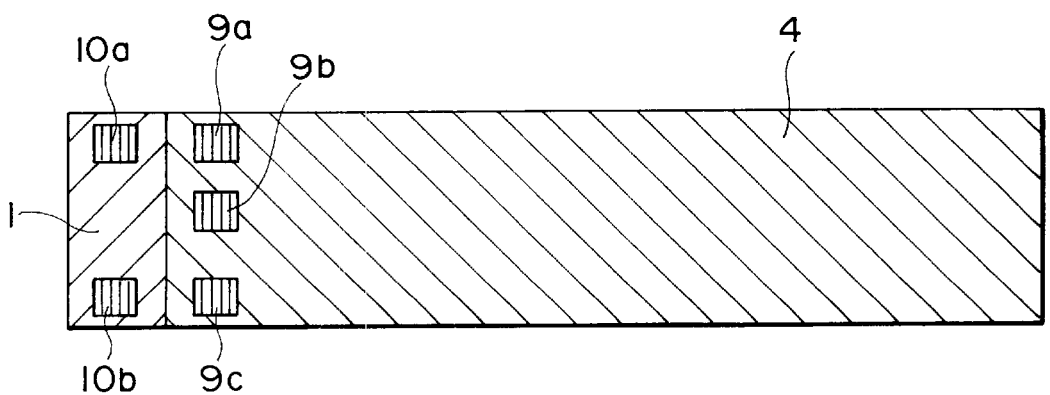
FIG. 2 is a plan view of the air/fuel ratio sensor according to the first embodiment.

FIG. 1 is a vertical sectional view showing a first embodiment of an air/fuel ratio sensor according to the present invention, and FIG. 2 is a plan view thereof, respectively.

As basic features of the air/fuel ratio sensor according to the present embodiment, the first resides in that an air/fuel ratio detector is formed of a laminated body A comprised of an oxygen reference electrode 6, a close or dense zirconia solid electrolyte 2, a negative electrode 7, a porous zirconia solid electrolyte 3, a positive electrode 8 and a porous protection film 4. The second resides in that the air/fuel ratio detector A and a ceramic substrate 1 with a heater 5 built therein are joined to each other in layered form and integrally formed. This type of air/fuel ratio sensor takes a structure in which a hollow chamber such as an air chamber seen in the conventional example is never included in the air/fuel ratio detector A.

In the present embodiment, the oxygen reference electrode 6 is interposed between the ceramic substrate 1 and the dense zirconia solid electrolyte 2, the negative electrode 7 is interposed between the dense zirconia solid electrolyte 2 and the porous zirconia solid electrolyte 3, and the positive electrode 8 is interposed between the porous zirconia solid electrolyte 3 and the protection film 4. However, these electrodes constitute the air/fuel ratio detector A so as to be put or biased to a longitudinally-extending one end of the laminated body A. Incidentally, the principle of operation thereof will be described later.

A plurality of pads 9 (corresponding to 9a, 9b and 9c in FIG. 2) are provided at an end of the laminated body A, which is located on the opposite side of the position corresponding to the air/fuel ratio detector. The pads 9a through 9c are provided to electrically connect the oxygen reference electrode 6, negative electrode 7 and positive electrode 8 to a signal processing circuit (not shown in the drawing) located outside the air/fuel ratio sensor (the details thereof will be explained using FIG. 3).

In the laminated body A having formed the air/fuel ratio detector and the ceramic substrate 1 with the heater built therein, the length of the ceramic substrate 1 is set so as to be slightly longer than that of the laminated body A, a step or step-like offset is ensured between the two, and pads 10 (corresponding to 10a and 10b in FIG. 2) are placed over the surface of the step. The pads 10 are provided to electrically connect the air/fuel ratio detector to a heater temperature control circuit (not shown in the drawing) for heating the air/fuel ratio detector to a predetermined temperature (700° C.) and controlling it.

Namely, the pads 10a and 10b disposed over the surface of the ceramic substrate 1 are electrically connected to the heater 5 via unillustrated through holes. Similarly, the pads 9a, 9b and 9c placed over the surface of the porous protection film 4 are respectively electrically connected to the positive electrode 8, oxygen reference electrode 6, and negative electrode 7 via through holes.

Figure 3:
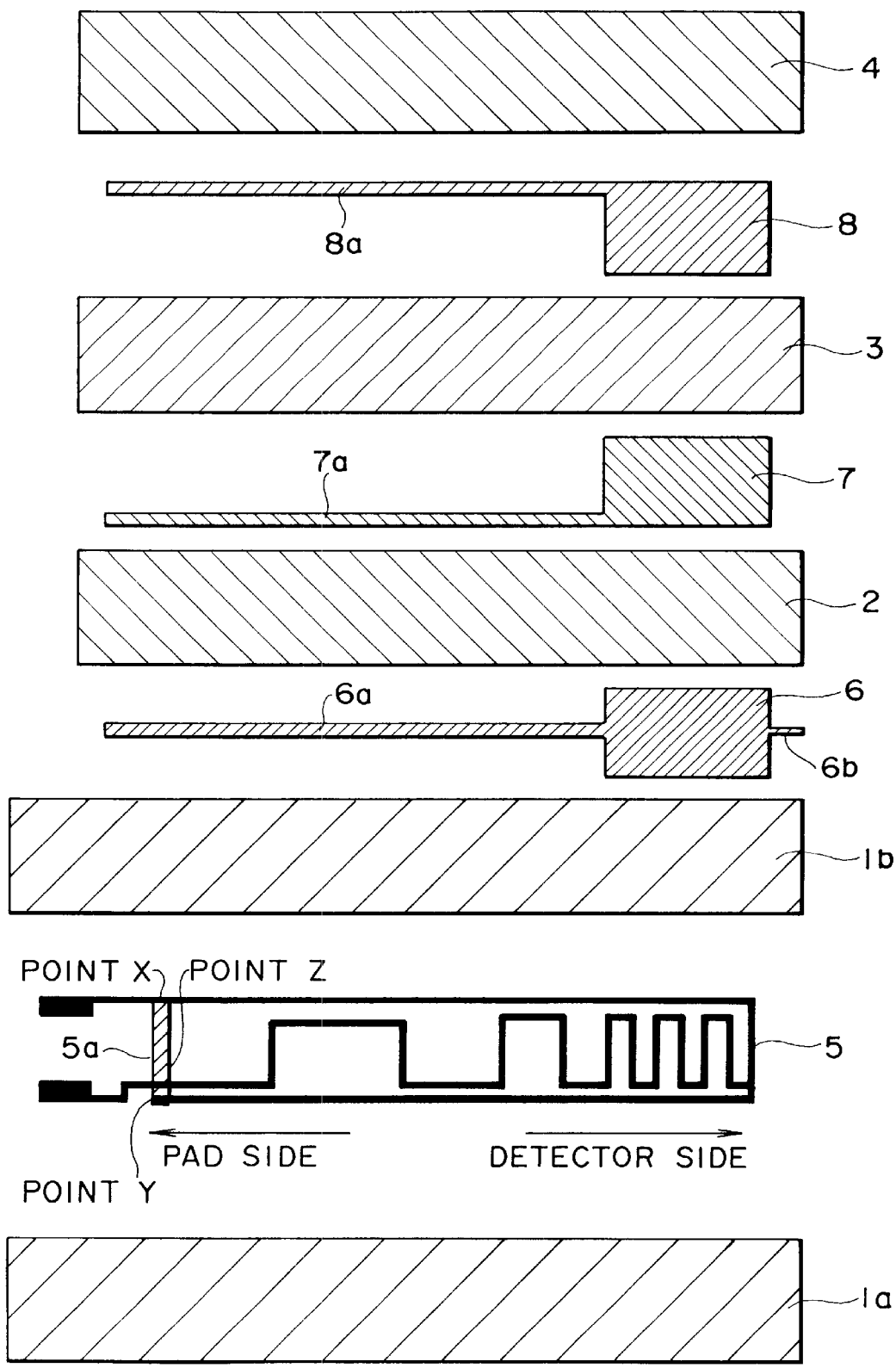
FIG. 3 is a developed view of the air/fuel ratio sensor according to the first embodiment.

A developed view of the air/fuel ratio sensor according to the present embodiment is shown in FIG. 3. A method of manufacturing the air/fuel ratio sensor according to the present embodiment will be explained in brief using the present drawing.

A ceramic substrate 1 is originally made up of two sheets of substrates 1a and 1b. A pattern for a heater 5 is printed over a green sheet-like ceramic substrate 1a composed of an insulating material such as alumina by a platinum base material having a thickness of several tens of microns. Points X and Y on the heater pattern are electrically connected to each other by a conductor 5a. Incidentally, the conductor 5a is not connected to a point Z on the heater pattern.

As shown in FIG. 3, the pattern for the heater 5 is elaborately formed on the air/fuel ratio detector side in the longitudinal direction of the laminated body A. However, it is shaped in the form of such a pattern as to gradually become less dense towards the pad side (the end of the air/fuel ratio detector on the opposite side thereof).

A green sheet-like ceramic substrate 1b is laminated on the heater 5. An oxygen reference electrode 6 composed of a platinum base metallic material having a thickness of a few microns is printed on the surface of the ceramic substrate 1b, and a green sheet-like dense zirconia solid electrolyte 2 containing yttria is stacked on the oxygen reference electrode 6. The printing of a negative electrode 7, the lamination of a porous zirconia solid electrolyte 3, the printing of a positive electrode 8 and the lamination of a porous protection film 4 composed of an insulating material such as spinel are successively carried out.

Here, the thickness of the ceramic substrate 1 is a value equivalent to about several hundred microns, the thicknesses of the dense zirconia solid electrolyte 2 and porous zirconia solid electrolyte 3 are respectively a value equivalent to about one hundred of microns, and the thickness of the porous protection film 4 is a value equivalent to about several tens of microns.

After the laminated body shown in FIG. 3 is thermocompressed with a suitable load, it is integrally calcined at a high temperature of about 1500° C. or higher. The oxygen reference electrode 6, negative electrode 7 and positive electrode 8 each composed of the platinum base metallic material are porously calcined so that their surface areas become extremely great, in order to activate a catalytic reaction with various exhaust gas components at such portions. Incidentally, whether or not the various members should be made dense or porous after their calcination, is determined depending on particle diameters or the like of these materials prior to their calcination. The oxygen reference electrode 6, negative electrode 7, and positive electrode 8 are connected to their corresponding pads 9b, 9c and 9a through leads 6a, 7a and 8a.

A pattern 6b having an extremely thin shape is formed at part (longitudinally-extending leading end) of the oxygen reference electrode 6. The thin shaped pattern 6b directly makes contact with an exhaust gas atmosphere through layer-to-layer spacing of the laminated body which constitutes the air/fuel ratio detector. This is because as will be described later, the oxygen fed to the oxygen reference electrode 6 by oxygen pump action is discharged into the exhaust gas atmosphere little by little through the thin pattern 6b to thereby control a pressure increase in oxygen partial pressure at this portion, whereby the air/fuel ratio detector is prevented from breaking.

Figure 4:
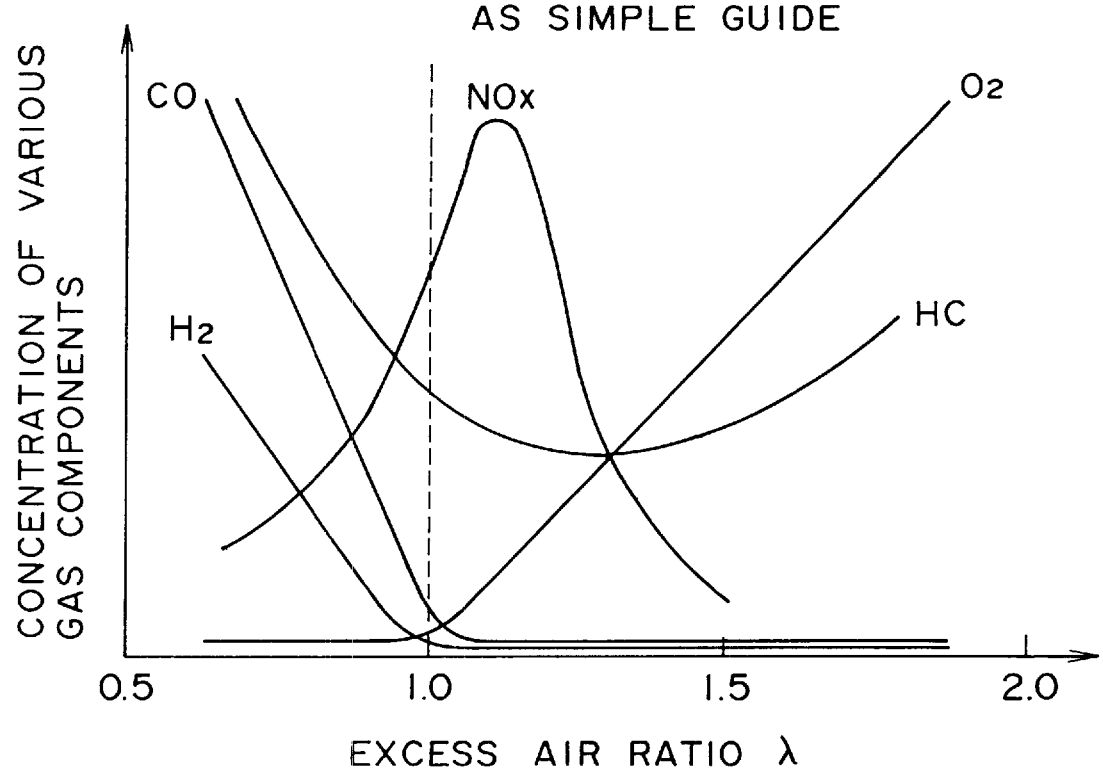
FIG. 4 is an explanatory view showing the relationship between an excess air ratio $\lambda$ and the concentrations of various exhaust gas components.
Figure 5:
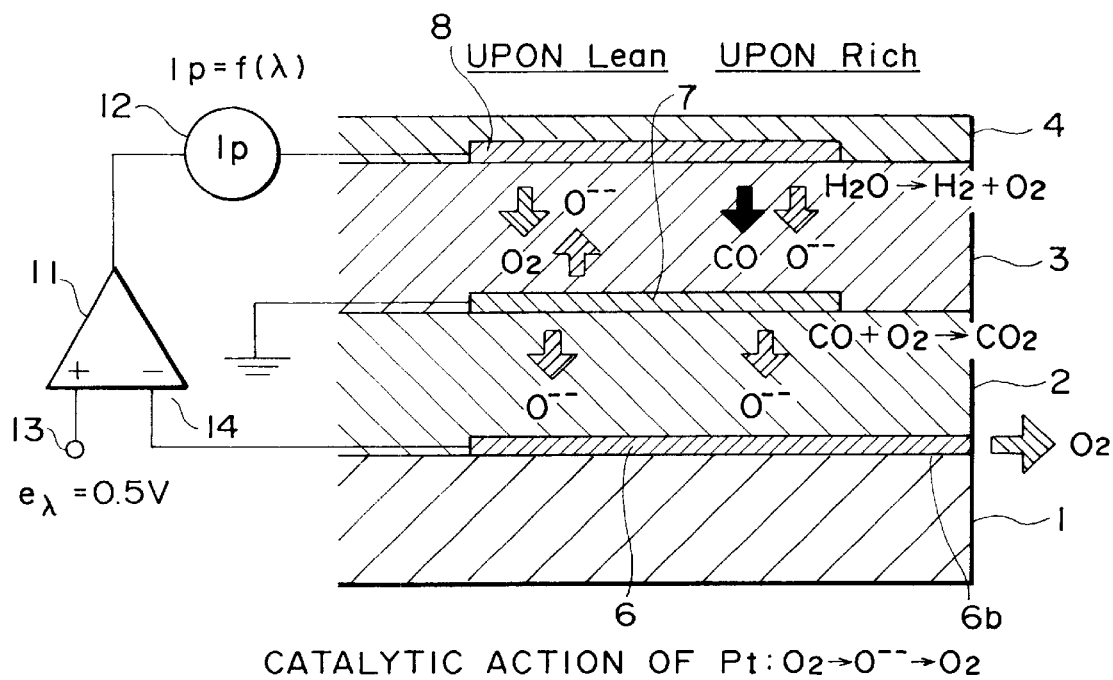
FIG. 5 is an explanatory view illustrating the detection principle of the air/fuel ratio sensor according to the present invention.

An air/fuel ratio detection principle of the present embodiment is shown in FIG. 5. The relationship between an excess air ratio λ and the concentrations of various exhaust gas components will be explained using FIG. 4 prior to the description of the present detection principle.

λ=1 shown in FIG. 4 indicates that the ratio between air and a fuel fed to a vehicle engine is a theoretical air/fuel ratio point. Namely, the theoretical air/fuel ratio is an inverse number of the ratio of the quality of the fuel fed to the engine to the flow rate or quality of air necessary to burn the fuel. As shown in the drawing, the concentration of $O_2$ increases in a lean (Lean) region of λ>1, and the concentrations of $H_2$ and CO corresponding to non-combustion gas components of the fuel increase in a rich (Rich) region of λ<1. In a Lean region in which λ slightly exceeds 1.0, the concentration of NOx reaches a maximum and the concentration of HC reaches a minimum. Incidentally, the concentrations of $O_2$, $H_2$ and CO in the present drawing are on the order of a few %, and the concentrations of NOx and HC are on the order of a few hundred ppm. The concentrations of these gas components on the vertical axis are shown as a simple guide.

As described in the detection principle of FIG. 5, the oxygen reference electrode 6 is connected to a − side input terminal 14 of a differential amplifier 11, the negative electrode 7 is connected to the ground, and the positive electrode 8 is connected to an output terminal of the differential amplifier 11 through a circuit 12 for detecting a pump current Ip.

A set value (e.g., 0.5V) corresponding to a predetermined electromotive force $e_\lambda$ is supplied to a + side input terminal 13 of the differential amplifier 11 to thereby control the difference in potential between the oxygen reference electrode 6 and the negative electrode 7 to $e_\lambda$. If the pump current Ip equivalent to oxygen ions ($O^{--}$), which flows between the positive electrode 8 and the negative electrode 7, is measured by the detection circuit 12 at this time, then this value results in the function of the excess air ratio λ. The flow of the oxygen ions flowing into the air/fuel ratio detector A will be explained below in detail with the Lean and Rich regions as examples (incidentally, no pump current Ip flows in a theoretical air/fuel ratio region λ=1). While only the oxygen ions flows into the dense zirconia solid electrolyte 2, the porous zirconia solid electrolyte 3 having an infinite number of extremely small holes allows the gas components such as $O_2$ as well as the oxygen ions to pass therethrough.

In the case of the Lean region (λ>1), $O_2$ flows into the negative electrode 7 by diffusion through the porous protection film 4 and the small holes of the porous zirconia solid electrolyte 3 in accordance with a diffusion controlled principle proportional to the difference in concentration between oxygen partial pressures (the porous protection film 4 and the porous zirconia solid electrolyte 3 constitute an exhaust gas diffusion controlled layer in that sense). The $O_2$ gas, which has flowed into the negative electrode 7, is converted into oxygen ions by catalytic action of the negative electrode 7 composed of a platinum base material.

Of the oxygen ions, a predetermined small amount of oxygen ions is fed to the oxygen reference electrode 6 side, and the majority of others is fed to the positive electrode 8 side. Since the amount of the oxygen ions, which move from the negative electrode 7 to the positive electrode 8 is proportional to the concentration of $O_2$ in an exhaust gas atmosphere, an excess air ratio λ at λ>1 can be detected from the pump current Ip measured by the detection circuit 12. On the other hand, the oxygen ions, which move from the negative electrode 7 to the oxygen reference electrode 6, are converted into $O_2$ by the oxygen reference electrode 6 and oxygen partial pressure at this portion is maintained at a predetermined value. Since the oxygen reference electrode 6 is always held at predetermined oxygen partial pressure or greater without depending on the state of operation of the engine, i.e., the value of the excess air ratio λ, this is why the present electrode is called an oxygen reference electrode. Since part of the porous oxygen reference electrode 6 makes contact with the exhaust gas atmosphere through the thin pattern 6b, $O_2$ flows out into an exhaust gas little by little through the thin pattern 6b. Further, a rise in oxygen partial pressure of the oxygen reference electrode 6 is controlled to prevent the breakage of the detector of the air/fuel ratio sensor.

In the Rich region (λ<1), $O_2$ is extremely low in the exhaust gas atmosphere and the concentrations of $H_2$ and CO corresponding to the non-combustion gas components increase. Further, the oxygen partial pressure of the negative electrode 7 is extremely reduced and the difference in potential (i.e., electromotive force) between the oxygen reference electrode 6 and the negative electrode 7 will increase up to near 1V. In order to prevent it, the electromotive force at the oxygen reference electrode 6 is controlled to the predetermined value $e_\lambda$ by the differential amplifier 11.

Therefore, the flow of the oxygen ions and non-combustion gases in the Rich region is as follows. The non-combustion gases such as $H_2$, CO, etc. flow into the negative electrode 7 by diffusion through the porous protection film 4 and the small holes of the porous zirconia solid electrolyte 3 in accordance with the diffusion controlled principle proportional to the difference in concentration between the gases. $O_2$, which reacts with these non-combustion gases, is fed from the positive electrode 8 to the negative electrode 7 in the form of the oxygen ions through the porous zirconia solid electrolyte 3 by an oxygen pump phenomenon. Namely, since no $O_2$ exists in the exhaust gas atmosphere in the Rich region, water vapor ($H_2O$) which exists in the exhaust gas in large quantities, is decomposed into $H_2$ and $O_2$ by catalytic action of the positive electrode 8 composed of the platinum base metallic material.

The decomposed $O_2$ is further converted to the oxygen ions by the positive electrode 8 and fed from the positive electrode 8 to the negative electrode 7 in the form of the oxygen ions through the porous zirconia solid electrolyte 3 as described above.

The oxygen ions fed from the positive electrode 8 to the negative electrode 7 are converted to $O_2$ again by the negative electrode 7. An extremely small amount of $O_2$ is fed to the oxygen reference electrode 6 by using the oxygen pump phenomenon in a manner similar to the Lean region, and oxygen partial pressure at this portion is held at a predetermined value. The remaining majority of $O_2$ reacts with the non-combustion gases such as $H_2$, CO, etc. which have flowed into the negative electrode 7 by diffusion through the porous protection film 4 and the small holes of the porous zirconia solid electrolyte 3. Further, $H_2$ is converted to water vapor and CO is converted to $CO_2$, respectively. The amount of $O_2$ fed from the positive electrode 8 to the negative electrode 7 is a value equal to the burned amount of the non-combustion gas components which have flowed into the negative electrode 7 by the diffusion controlled phenomenon. Therefore, the amount of the oxygen ions, which move from the positive electrode 8 to the negative electrode 7 (flow in the direction opposite to that in the Lean region), i.e., a pump current Ip is measured by the detection circuit 12, whereby an excess air ratio $\lambda$ in the Rich region can be detected accurately.

If the pump current Ip in the Lean region ($\lambda>1$) is defined as positive, then the value of the Rich region ($\lambda<1$) becomes negative. Further, it becomes zero at the theoretical air/fuel ratio ($\lambda=1$)

According to the present embodiment, the formation of all of the air/fuel ratio detector and the heater as the laminated structure excluding the hollow chamber allows the air/fuel ratio sensor to operate in a short time (about 5 seconds or less) after power-on. Further, a temperature gradient produced in the direction of the thickness of the detector of the air/fuel ratio Sensor is reduced and hence a thermal stress developed due to the temperature gradient can be reduced. Since no hollow chamber exists, a warpage-free laminated body can be obtained.

Further, a thermal stress developed in the longitudinal direction of the air/fuel ratio sensor can be also reduced by a heater pattern which makes slow a temperature gradient developed in the longitudinal direction of the air/fuel ratio sensor.

Figure 9:
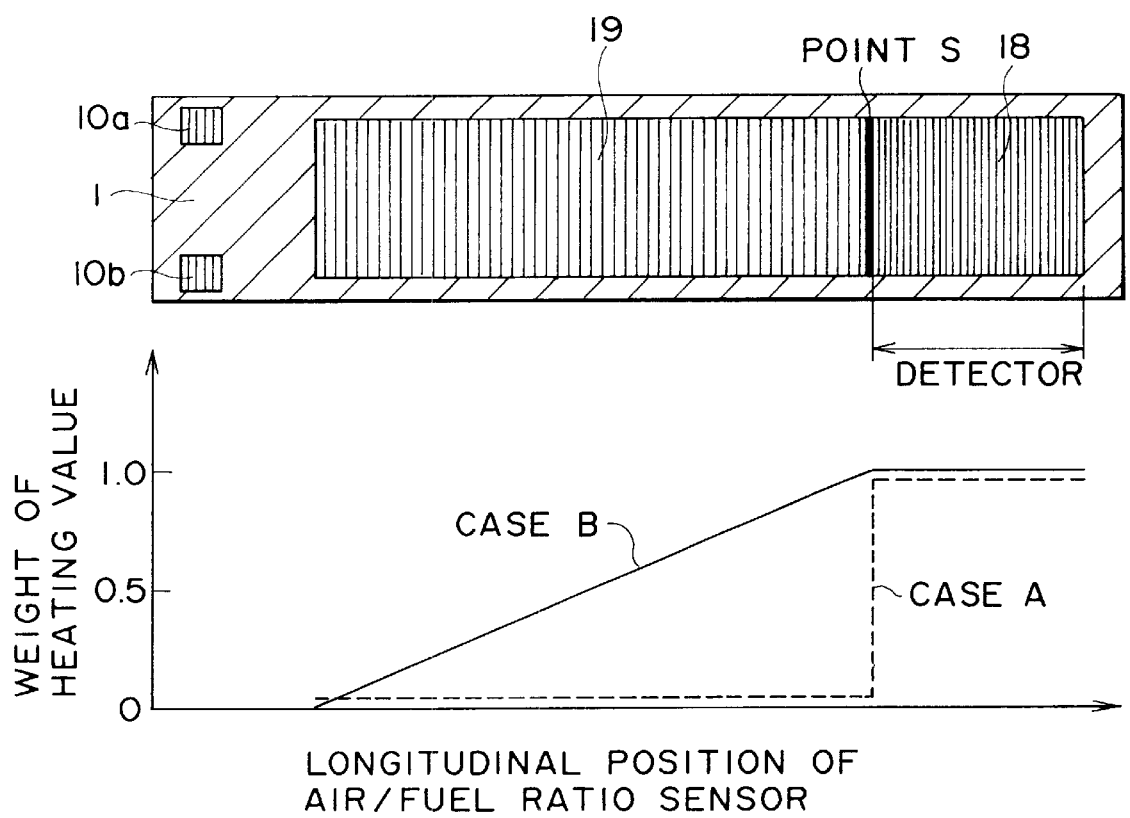
FIG. 9 is an explanatory view illustrating a heater pattern applied to the respective embodiments.

A view for explaining the above-described heater pattern is shown in FIG. 9. Regions for the heater pattern are respectively defined as a region 18 at a portion just below the air/fuel ratio detector and a region 19 at another portion. Let's consider a case A and a case B as the generated amount of heat or heating values of the heater 5. The case A indicated by a dotted line corresponds to a case in which a heater pattern is designed so that heat is principally generated only in the region 18. In this case, an extremely large temperature gradient is produced in the longitudinal direction of the air/fuel ratio sensor. A crack was apt to occur in the vicinity of a point S in the drawing due to a thermal stress developed by the temperature gradient. The case B indicated by a solid line is a case in which the heater is heated even in the region 19 and a heater pattern is designed so that a heating value thereof gradually decreases gently as it moves toward the pad side (the pattern for the heater 5, which is shown in FIG. 3, corresponds to the case B in the present drawing). By doing so, the temperature gradient in the longitudinal direction of the air/fuel ratio sensor becomes gentle, and hence the thermal stress developed in the laminated structure of the sensor can be set to a very small value.

As a result, a combined air/fuel ratio sensor free from the occurrence of any crack and having a high degree of reliability could be obtained.

Figure 6:
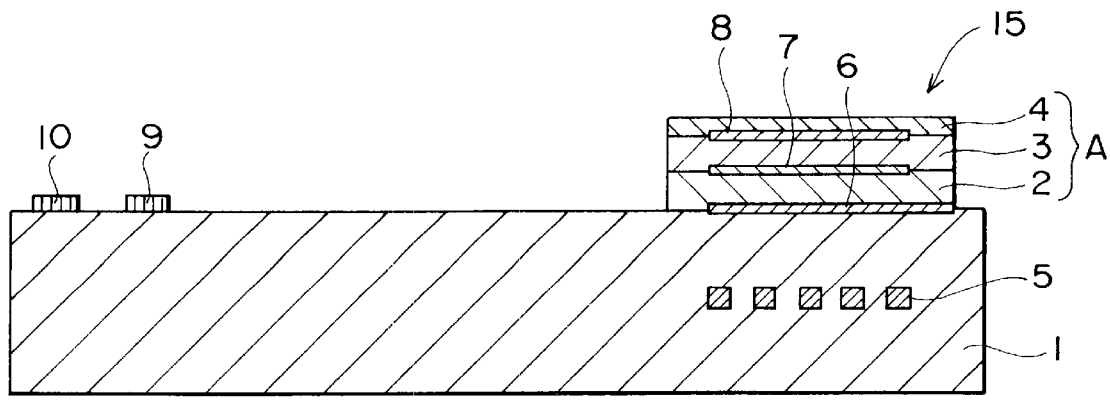
FIG. 6 is a vertical sectional view depicting a second embodiment of an air/fuel ratio sensor according to the present invention.
Figure 7:
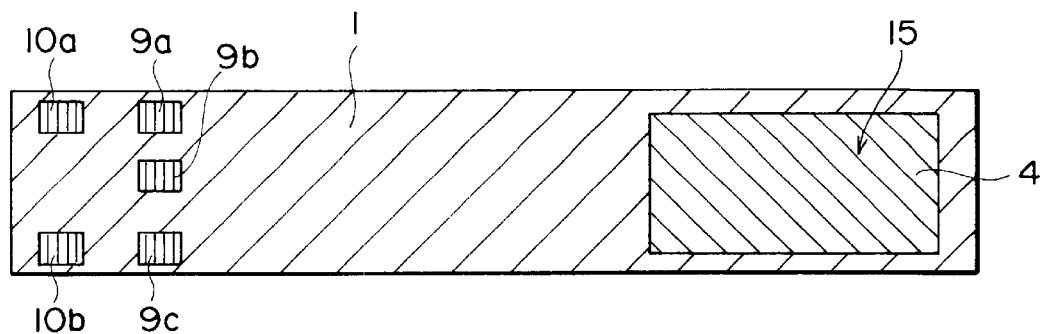
FIG. 7 is a plan view of the air/fuel ratio sensor according to the second embodiment.

FIG. 6 is a vertical sectional view showing a second embodiment of an air/fuel ratio sensor according to the present invention. Incidentally, the same reference numerals as those employed in the first embodiment in the drawing indicate the same or common elements (drawings to be illustrated subsequently are also similar to it). FIG. 7 is a plan view of the air/fuel ratio sensor according to the present embodiment.

As shown in these drawings, a laminated body A, which constitutes an air/fuel ratio detector 15, is formed on a longitudinally-extending one end (leading end) of a ceramic substrate 1. Further, pads (9a through 9c) and 10 (10a and 10b) are disposed over the ceramic substrate 1 on the side opposite to the position where the laminated body A is provided. A basic configuration of the air/fuel ratio detector 15 is similar to that employed in the first embodiment.

The present embodiment is one in which the air/fuel ratio detector 15 (laminated body A) is printed on a part of the surface of the green sheet-like ceramic substrate 1 having a heater built therein and a thickness of at least 500 microns or more. Namely, an oxygen reference electrode 6, a dense zirconia solid electrolyte 2, a negative electrode 7, a porous zirconia solid electrolyte 3, a positive electrode 8 and a porous protection film 4 are all laminated successively over the thick ceramic substrate 1 by printing. Here, the thickness of each of the dense zirconia solid electrolyte 2, porous zirconia solid electrolyte 3 and porous protection film 4 is a thin thickness which ranges from several tens of microns to several hundred microns.

According to the present embodiment, an effect similar to that obtained in the first embodiment can be brought about. Further, even if a pattern for a heater 5 is centralized just below the air/fuel ratio detector, a thermal stress can be reduced because the laminated body A is short. Besides, the formation and placement of the heater pattern can be simplified.

Since the laminated body A is formed by printing, the air/fuel ratio detector (laminated body) can be formed thin as compared with the green sheet. Therefore, the time required to add heat from the heater and transfer it can be advanced as compared with the green sheet type, whereby the time required to start the sensor (activate it) can be reduced.

Further, the printing type can reduced in installation cost as compared with the type for sintering the green sheet, and the manufacturing cost of the air/fuel ratio sensor can be also reduced.

Figure 8:
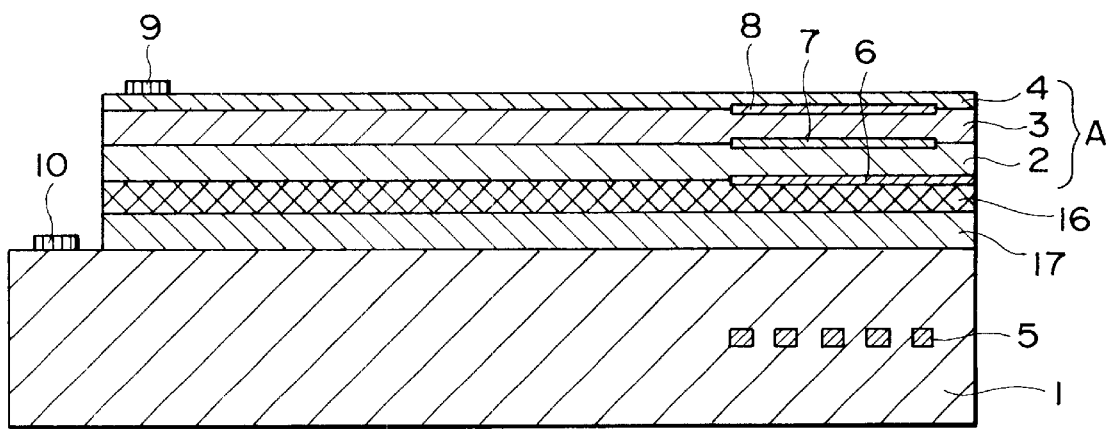
FIG. 8 is a vertical sectional view showing a third embodiment of an air/fuel ratio sensor according to the present invention.

FIG. 8 is a vertical sectional view of an air/fuel ratio sensor according to a third embodiment of the present invention.

In the present embodiment, the structure of the present air/fuel ratio sensor is different from that of the air/fuel ratio sensor shown in FIG. 1 in the following points. Namely, insert members (thermal stress buffer layers) 16 and 17 each having an intermediate coefficient of thermal expansion between alumina and a zirconia solid electrolyte are disposed between a ceramic substrate 1 having a heater 5 built therein and composed of an alumina material and a laminated body A (corresponding to a laminated body comprised of a dense zirconia solid electrolyte 2, a porous zirconia solid electrolyte 3 and a porous protection film 4) serving as an air/fuel ratio detector. The insert members do no necessarily require two layers.

In the present embodiment, the insert member 17 is a material close in thermal expansion coefficient to the ceramic substrate 1, whereas the insert member 16 is a material close in thermal expansion coefficient to the dense zirconia solid electrolyte 2. The thermal expansion coefficients of these insert members are determined according to the ratio of the quality of alumina to the quality of zirconia. Namely, the insert member 17 is composed of a material in which the quality of alumina is increased, and the insert member 16 is composed of a material in which the quality of zirconia is increased.

According to the present embodiment, the following functions and effects can be brought about in addition to the attainment of an effect similar to that obtained in the first embodiment.

Namely, the insert members each having the intermediate thermal expansion coefficient between the ceramic substrate 1 having the heater 5 built therein and the zirconia solid electrolyte 2 are placed therebetween, and the insert members are divided into plural forms and the ratio of the quality of alumina to the quality of zirconia is set to plural steps, whereby a thermal stress developed in the laminated body serving as the detector for the air/fuel ratio sensor can be reduced more effectively. As a result, a high-reliable air/fuel ratio sensor which prevents a crack from occurring in the detector, can be provided.

Figure 10:
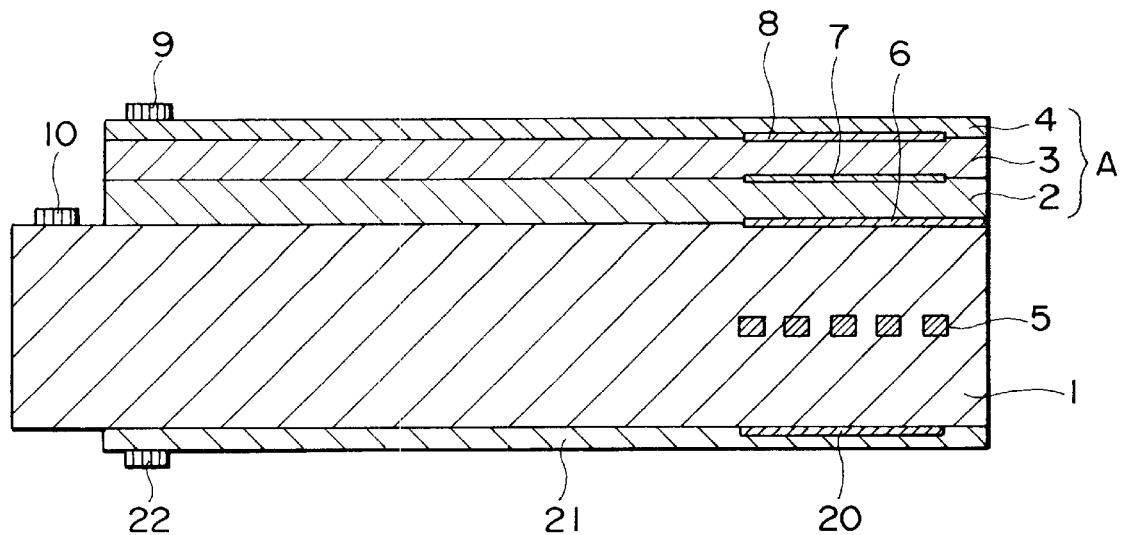
FIG. 10 is a vertical sectional view depicting a fourth embodiment of an air/fuel ratio sensor according to the present invention.

FIG. 10 is a vertical sectional view of an air/fuel ratio sensor according to a fourth embodiment of the present invention. In the present embodiment, the structure of the present air/fuel ratio sensor is different from that of the air/fuel ratio sensor shown in FIG. 1 in the following point.

Namely, it resides in that an oxide semiconductor 20 covered with a porous protection film 21 is formed over one surface of a ceramic substrate 1 having a heater 5 incorporated therein, and a pad 22 for connecting the oxide semiconductor 20 to an externally provided signal processing circuit is provided over the surface of the porous protection film 21.

The oxide semiconductor 20 is used to detect the concentrations of HC and NOx in an exhaust gas atmosphere and varies in its electrical resistance value according to the concentrations of HC and NOx. The present embodiment takes a structure in which no hollow chamber is provided even at an exhaust gas detector for detecting HC, NOx, etc. together with a detector for the air/fuel ratio sensor. By doing so, a temperature gradient developed in the direction of the thickness of the detector for the combined air/fuel ratio sensor becomes small and hence a thermal stress developed due to the temperature gradient is reduced. A warpage-free laminated body can be obtained because of the absence of the hollow chamber. As a result, a crack-free and high-reliability combined air/fuel ratio sensor in which the exhaust gas detector for detecting HC, NOx, etc. is brought into integration with the detector for the air/fuel ratio sensor, can be obtained. The combined air/fuel ratio sensor according to the present invention can construct a combustion control system capable of easily clearing the strict emission control applied immediately after the starting of a vehicle engine.

Figure 11:
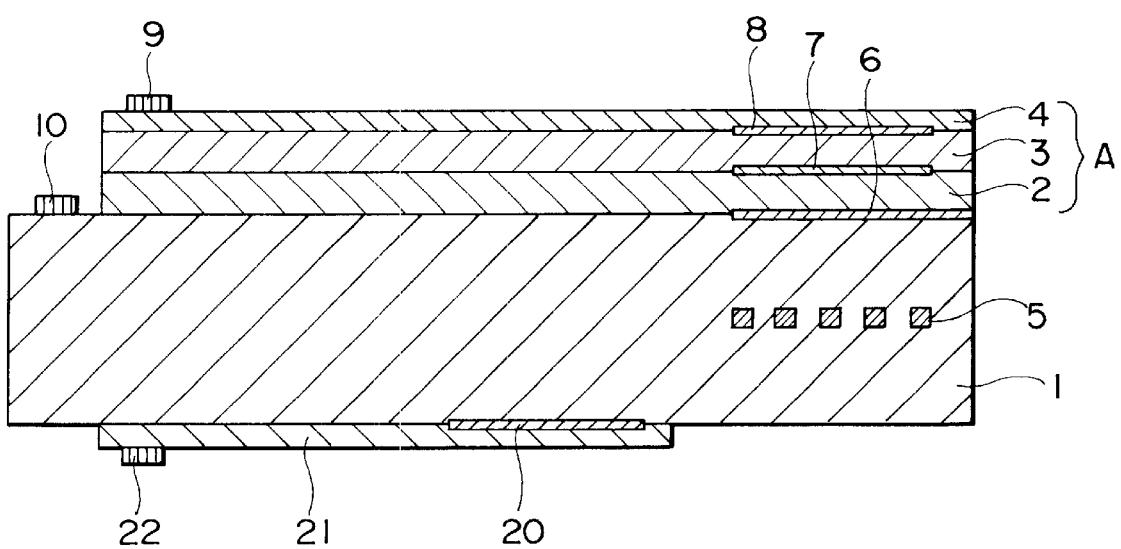
FIG. 11 is a vertical sectional view showing a fifth embodiment of an air/fuel ratio sensor according to the present invention.

FIG. 11 is a vertical cross-sectional view of an air/fuel ratio sensor showing a fifth embodiment according to the present invention.

The present embodiment is different from the embodiment shown in FIG. 10 in the following points.

An oxide semiconductor 20, which serves as an exhaust gas detector, is an example in which it is disposed at a portion placed under a relatively low temperature (of from 400° C. to 500° C.), of one surface of a ceramic substrate 1 so as to avoid a portion just below a heater 5. The optimum operating temperature of the oxide semiconductor for detecting the concentrations of HC and NOx varies according to its materials. The previous drawing shows a case in which the most suitable operating temperature of the oxide semiconductor is a high temperature (about 700° C.) in the same manner as the detector for the air/fuel ratio sensor. On the other hand, the present drawing shows a packed or mounted structure in which the optimum operating temperature is a low temperature (of from 400° C. to 500° C.).

Figure 12:
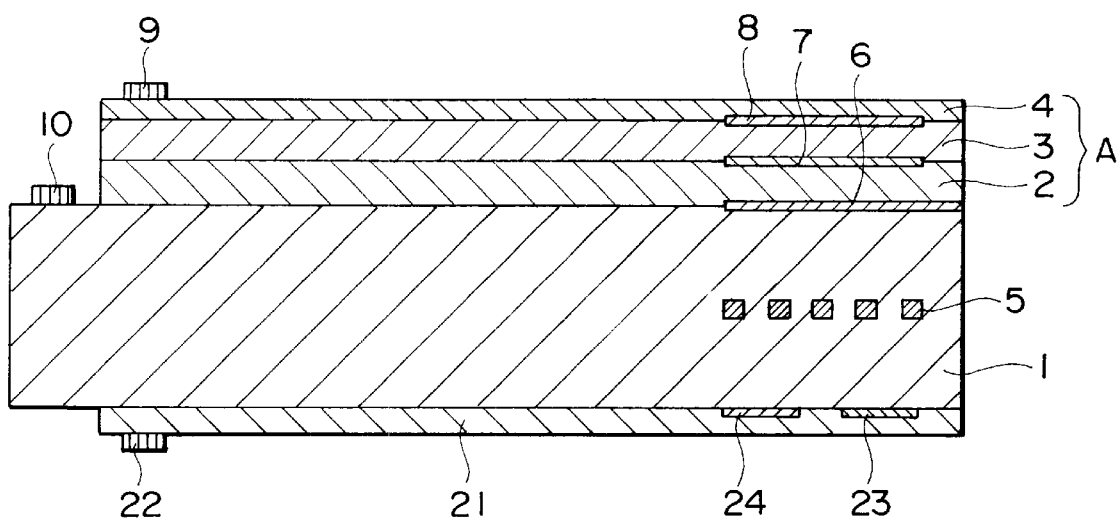
FIG. 12 is a vertical sectional view illustrating aسsixth embodiment of an air/fuel ratio sensor according to the present invention.

FIG. 12 is a vertical sectional view of an air/fuel ratio sensor showing a sixth embodiment according to the present invention.

The present embodiment is different from the embodiments shown in FIGS. 10 and 11 in that both an oxide semiconductor 23 for detecting the Concentration of NC and an oxide semiconductor 24 for detecting the concentration of NOx are brought into integration over one surface of a ceramic substrate 1 provided on the side opposite to the formed side of a laminated body A which serves as an air/fuel ratio detector, thereby constructing a combined air/fuel ratio sensor.

The exhaust gas detectors used for HC, NOx, etc., of the combined air/fuel ratio sensors illustrated in FIGS. 10 through 12 respectively show the embodiments each of which makes use of a change in resistance value of the oxide semiconductor due to these exhaust gas components.

A seventh embodiment of the present invention will next be explained using FIG. 13.

The present embodiment is intended for the detection of exhaust gas components such as HC, NOx, etc. by making use of an oxygen pump phenomenon of a zirconia solid electrolyte and a diffusion controlled phenomenon of HC, NOx, etc. in a porous member. The present embodiment is a combined air/fuel ratio sensor obtained by bringing such an exhaust gas detector into integration (lamination) together with the detector for the air/fuel ratio sensor according to each of the aforementioned embodiments.

The structure of the present embodiment is different from that of the air/fuel ratio sensor shown in FIG. 1 in the following point.

Namely, it resides in that an NOx detector comprised of a dense zirconia solid electrolyte 25, an NOx detecting electrode 27 and a porous oxide 26 is placed between a ceramic substrate 1 having a heater 5 built therein and a laminated body A (corresponding to a laminated body comprised of a dense zirconia solid electrolyte 2, a porous zirconia solid electrolyte 3 and a porous protection film 4) constituting an air/fuel ratio detector.

Figure 13:
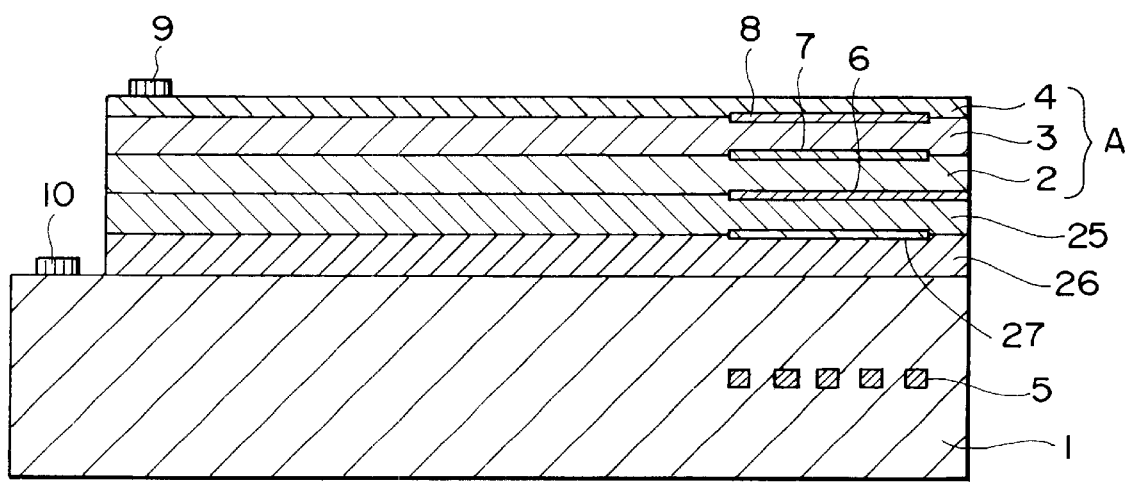
FIG. 13 is a vertical sectional view showing a seventh embodiment of an air/fuel ratio sensor according to the present invention.
Figure 14:
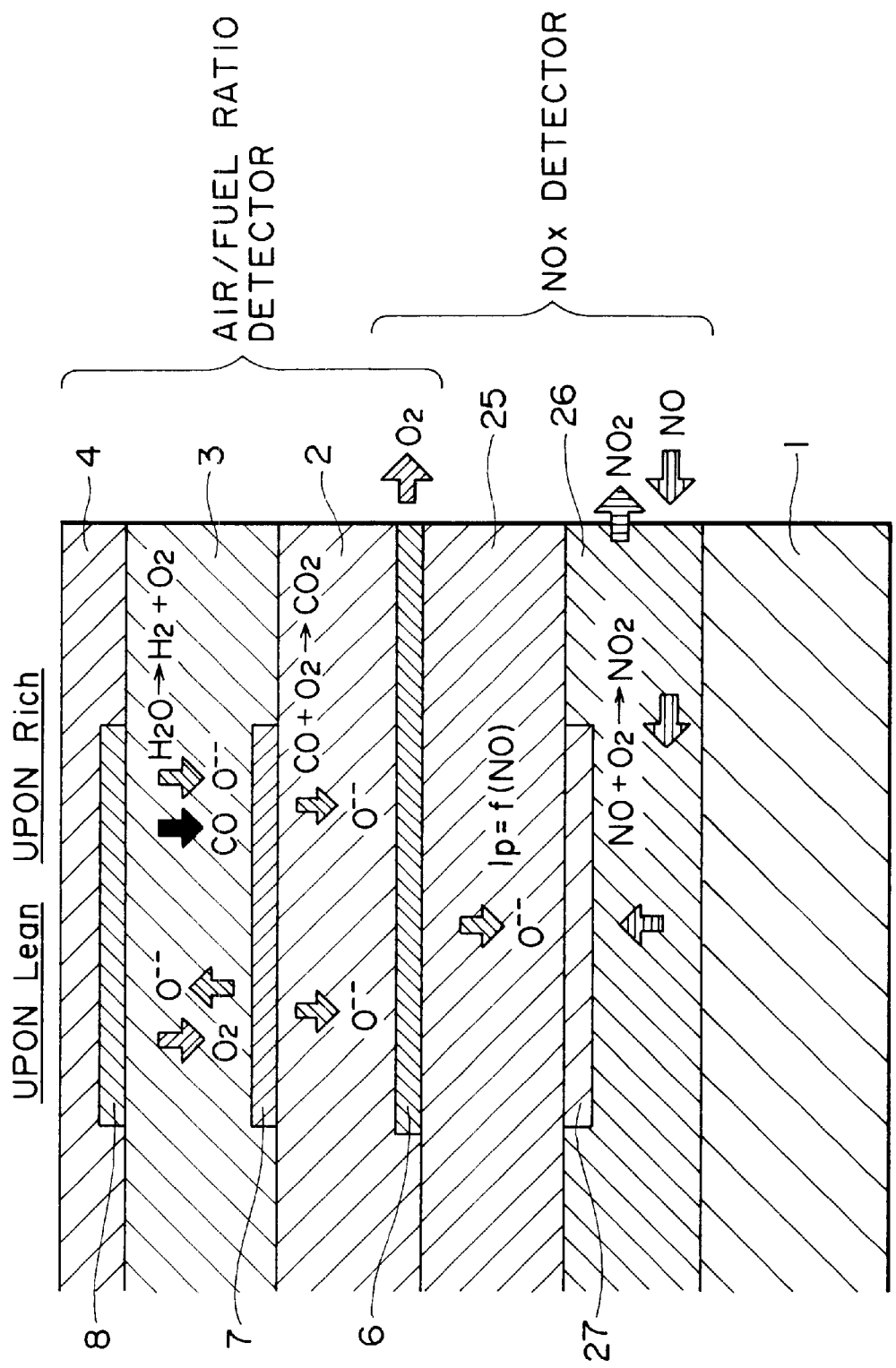
FIG. 14 is a view illustrating the detection principle of an NOx detector shown in FIG. 13.

A detection principle of the NOx detector of the combined air/fuel ratio sensor shown in FIG. 13 is shown in FIG. 14. A detection principle of the air/fuel ratio detector is shown in the present drawing together with the detection principle of the NOx detector. Since the detection principle of the latter air/fuel ratio detector has been described in FIG. 5, only the detection principle of the former NOx detector will be described herein.

The concentrations of various exhaust gas components can be detected with high sensitivity and selectively by suitably selecting materials for the electrode 27 and porous oxide 26.

It was found that when, for example, a platinum base metallic material was selected for the electrode 27 and porous $CdCr_2O_4$ was selected for the oxide 26, then the concentration of NO in an exhaust gas atmosphere could be detected selectively. NO flows into the surface of the NOx detecting electrode 27 by diffusion from within an exhaust gas flowing into the porous oxide 26 through the porous oxide 26. When a voltage (about 0.1V) is applied between the NOx detecting electrode 27 and an oxygen reference electrode 6 of the air/fuel ratio detector, oxygen ions move into the dense zirconia solid electrolyte 25 from the oxygen reference electrode 6 to the NOx detecting electrode 27 by an oxygen pump phenomenon.

Further, the oxygen ions are converted to $O_2$ by the NOx detecting electrode 27, which in turn reacts with NO which has flowed by diffusion. NO substitutes for $NO_2$ and flows into the exhaust gas, If, at this time, a pump current Ip corresponding to the oxygen ions which move into the dense zirconia solid electrolyte 25, is measured by an externally provided detection circuit, then the pump current Ip is proportional to the concentration of NO. Since no hollow chamber is provided even within the sensor having such a structure, a combined air/fuel ratio sensor free from the occurrence of any crack and having a high degree of reliability can be obtained. Incidentally, it was found that the Concentration of HC other than NOx could be detected selectively by suitably selecting the materials for the electrode 27 and the porous oxide 26.

Figure 15:
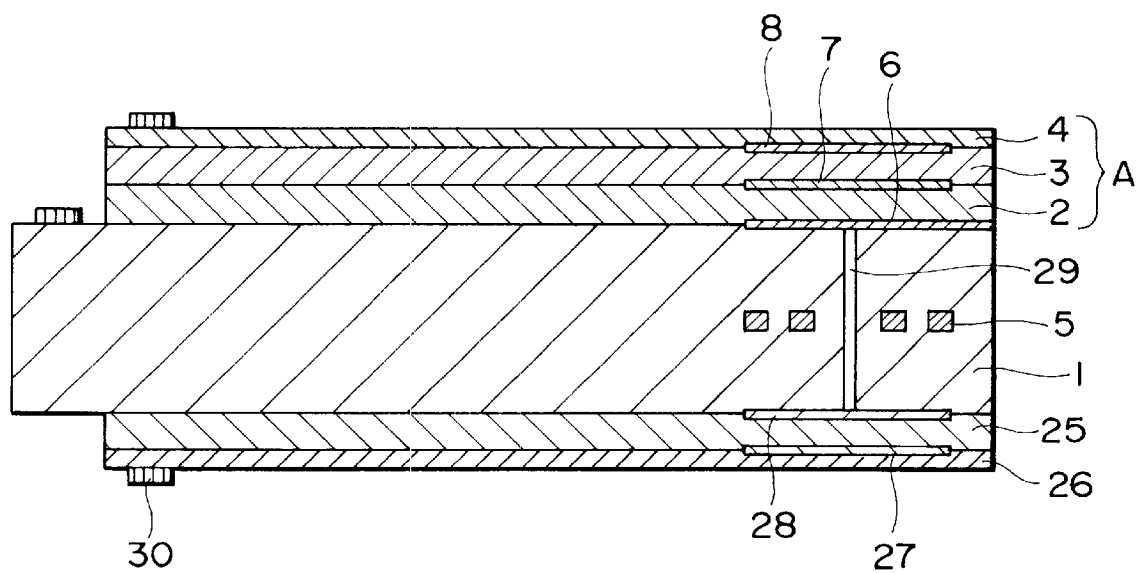
FIG. 15 is a vertical sectional view depicting an eighth embodiment of an air/fuel ratio sensor according to the present invention.

FIG. 15 is a vertical cross-sectional view showing an embodiment (eighth embodiment) of a combined air/fuel ratio sensor according to the present invention.

The present embodiment is a sensor having the same principle as that of the combined air/fuel ratio sensor shown in FIG. 13 although it is different therefrom in structure.

The present embodiment is different from the combined air/fuel ratio sensor referred to above in that an NOx detector is implemented on another surface (corresponding to the surface on the side opposite to the provision side of a laminated body A constituting an air/fuel ratio detector) of a ceramic substrate 1 with a heater 5 built therein.

Namely, the air/fuel ratio detector obtained by stacking an oxygen reference electrode 6, a dense zirconia solid electrolyte 2, a negative electrode 7, a porous solid electrolyte 3, a positive electrode 8, and a porous protection film 4 on one another is formed on one surface of the ceramic substrate 1 having the heater 5 built therein. The NOx detector obtained by laminating an oxygen reference electrode 28, a dense zirconia solid electrolyte 25, an NOx detecting electrode 27 and a porous oxide 26 on one another is formed on the other surface of the ceramic substrate 1. The oxygen reference electrode 6 of the air/fuel ratio detector and the oxygen reference electrode 28 of the NOx detector communicate with each other so as to allow an oxygen gas to conduct or make continuity via a through hole 29 defined in the ceramic substrate 1. $O_2$ lying on the side of the oxygen reference electrode 6 of the detector for the air/fuel ratio sensor can be diffused into the electrode 28 of the NOx detector via the through hole 29 provided so as to extend through the ceramic substrate 1.

As a result, the electrode 28 can also have the function of the oxygen reference electrode. Incidentally, the NOx detector is electrically connected to an externally provided detection circuit through a pad 30 provided over the porous oxide 26.

Figure 16:
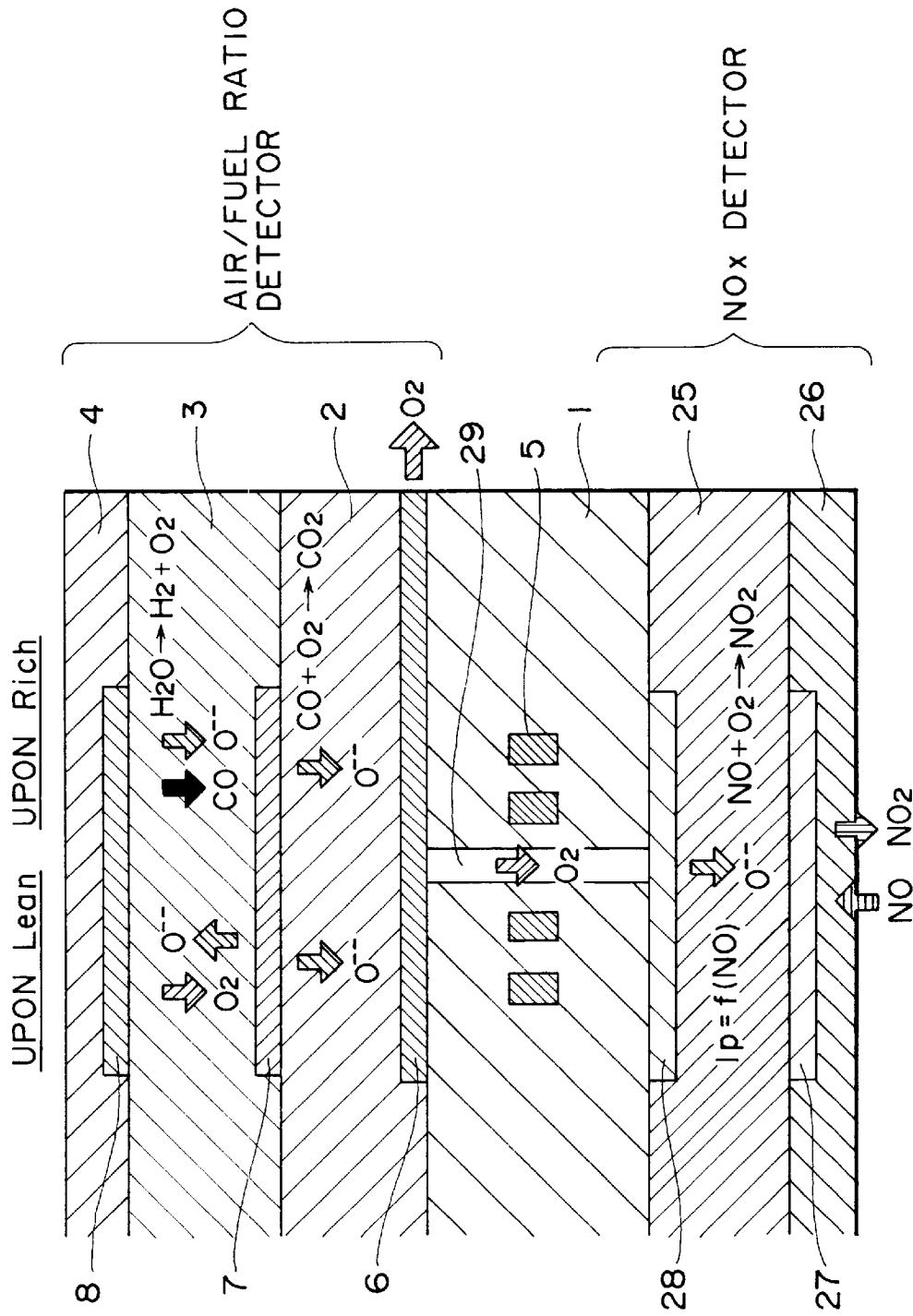
FIG. 16 is a view showing the detection principle of an NOx detector shown in FIG. 15.

A detection principle of the NOx detector of the combined air/fuel ratio sensor shown in FIG. 15 is shown in FIG. 16 together with that of the air/fuel ratio detector. Since the detection principle of the NOx detector is the same as that shown in FIG. 14, the description thereof will be omitted herein.

Figure 17:
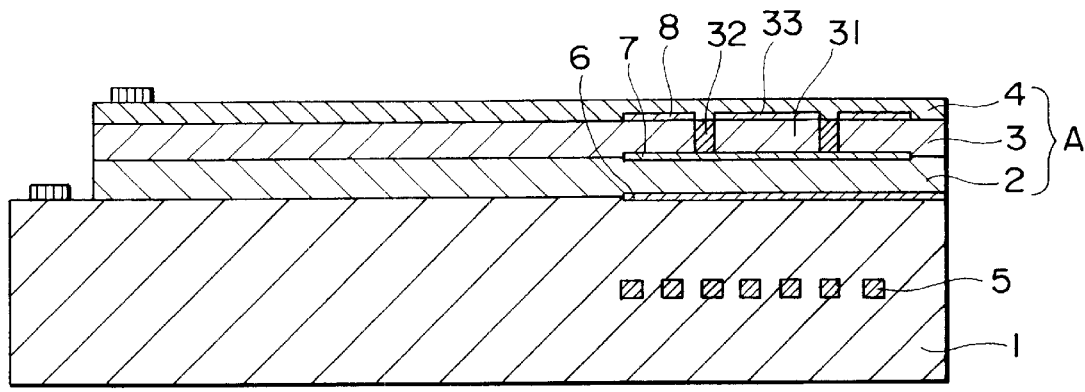
FIG. 17 is a vertical sectional view illustrating a ninth embodiment of an air/fuel ratio sensor according to the present invention.

FIG. 17 is a vertical sectional view showing an embodiment (ninth embodiment) of a combined air/fuel ratio sensor according to the present invention.

The present embodiment is one wherein an NOx detector is disposed in the air/fuel ratio detector (laminated body A) of the air/fuel ratio sensor shown in FIG. 1. Namely, part of a porous zirconia solid electrolyte 3 is hollowed or cut out, a dense zirconia solid electrolyte 31 surrounded by dense insulating materials 32 is placed in the cut portion, and an electrode 33 composed of a platinum base metallic material is deposited or grown over the upper surface of the dense zirconia solid electrolyte 31.

Figure 18:
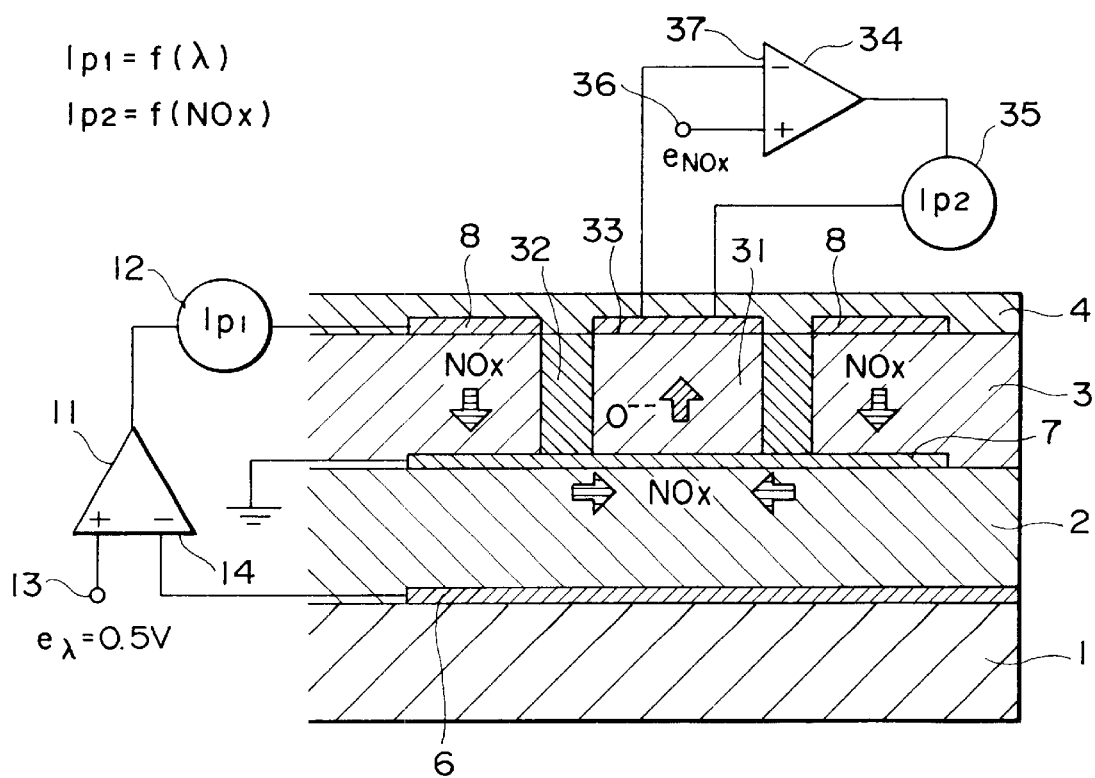
FIG. 18 is a view showing the detection principle of an NOx detector shown in FIG. 17.

A detection principle of the NOx detector of the combined air/fuel ratio sensor shown in FIG. 17 is illustrated in FIG. 18. A detection principle of the air/fuel ratio detector is also shown in the drawing together with that of the NOx detector. Since the detection principle of the latter air/fuel ratio detector has been described in FIG. 5, only the detection principle of the former NOx detector will be described.

NOx, which has diffused into a porous zirconia solid electrolyte 3 so as to flow into a negative electrode 7, is next diffused into a porous portion of the negative electrode 7 so as to reach a portion below the dense zirconia solid electrolyte 31. A − side input terminal 37 of a differential amplifier 34 and the electrode 33 are connected to each other and a predetermined electromotive force $e_{NOx}$ is supplied to a + side input terminal 36. The differential amplifier 34 electrically controls the NOx detector so that the difference in potential between the electrode 33 and the negative electrode 7 becomes $e_{NOx}$. At this time, NOx, which has flowed into the negative electrode 7 by diffusion, is decomposed so that an $O_2$ gas is generated. This $O_2$ is converted to oxygen ions by the negative electrode 7, which in turn pass through the dense zirconia solid electrolyte 31 so as to move from the negative electrode 7 to the electrode 33. If a pump current Ip2 corresponding to the amount of the oxygen ions is measured by a detection circuit 35, then this value results in a value proportional to the concentration of NOx. Since no hollow chamber exists in the present NOx detector, a high-reliable combined air/fuel ratio sensor can be obtained in which the NOx detector is brought into integration together with the detector for the air/fuel ratio sensor.

Figure 19:
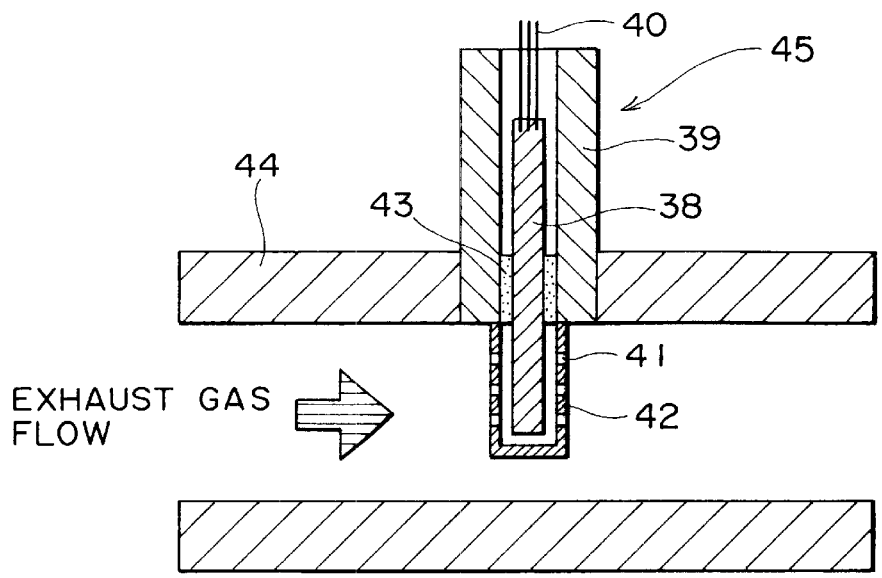
FIG. 19 is a view illustrating a schematic mounting method for the air/fuel ratio sensors according to the respective embodiments.

A method for schematically implementing the air/fuel ratio sensor according to each of the aforementioned embodiments is shown in FIG. 19.

A laminated body 38, which constitutes a detector of an air/fuel ratio sensor 45, is hermetically fixed to a housing 39 by means of jointing materials 43 at an intermediate position between the detector and a pad. The laminated body 38 of the air/fuel ratio sensor 45 is connected to an externally provided signal processing circuit and the like through a plurality of lead wires 40. When the combined air/fuel ratio sensor 45 is attached to an exhaust pipe 44, the flow of an exhaust gas passes through small holes 41 of a louver 42 provided at the tip of the housing 39 so as to reach the detector of the laminated body 38 of the combined air/fuel ratio sensor 45.

Figure 20:
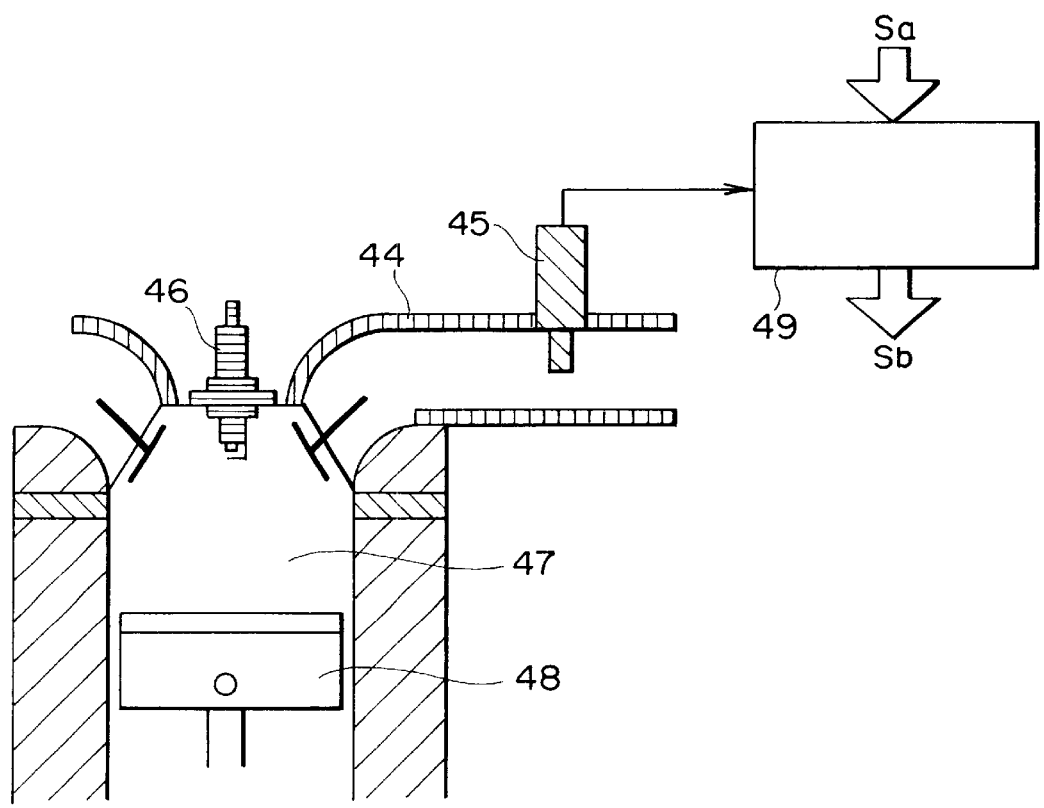
FIG. 20 is a view showing a schematic configuration of an engine control system which utilizes the air/fuel ratio sensor according to each of the respective embodiments.

A schematic configuration of an engine control system using a combined air/fuel ratio sensor according to the present invention is shown in FIG. 20. A mixed gas of air and a fuel fed into a combustion chamber 47 is ignited by an ignition plug 46 upon a compression stroke during which a piston 48 has been elevated. A post-combustion exhaust gas reaches a combined air/fuel ratio sensor 45 through an exhaust pipe 44. An air/fuel ratio corresponding to the ratio between the air and fuel fed to an engine, and the concentrations of exhaust gas components such as NOx, HC, etc. are detected by the combined air/fuel ratio sensor 45. A signal outputted from the combined air/fuel ratio sensor 45 is fed to a microcomputer 49 used for the control of the engine. The microcomputer 49 processes the signal inputted from the combined air/fuel ratio sensor 45 and signals Sa inputted from various sensors and outputs an output signal Sb for driving various actuators starting with an injector for supplying the fuel to the engine.

Since the air/fuel ratio sensor according to the present invention is short in starting time in particular, a combustion control system suitable for use in the engine, which is capable of easily clearing the emission control applied immediately after the starting of the engine, can be provided.

According to the present invention as described above, a high-reliable air/fuel ratio sensor, which is operated in a short time (about 5 seconds) after power-on so as to comply with emission control applied immediately after startup by increasing heating rates of an air/fuel ratio detector, an exhaust gas components detector, etc. and which is capable of detecting an air/fuel ratio lying in a Lean-Rich range with low power consumption and with a laminated structure in which a hollow chamber is excluded so as to achieve the prevention of a thermal crack and warpage, and an easy-to-implement complex or combined air/fuel ratio sensor capable of detecting even exhaust gases such as NOx, HC, etc. can be provided.

While the present invention has been described with reference to the illustrative embodiments, this description is not intended to be construed in a limiting sense. Various modifications of the illustrative embodiments, as well as other embodiments of the invention, will be apparent to those skilled in the art on reference to this description. It is therefore contemplated that the appended claims will cover any such modifications or embodiments as fall within the true scope of the invention.

What is claimed is:

1. An air/fuel ratio sensor, comprising:

an air/fuel ratio detector comprised of a laminated body formed by stacking an oxygen reference electrode, a dense solid electrolyte, a negative electrode, a porous solid electrolyte, a positive electrode, and a porous protection film on one another; and a ceramic substrate having a heater built therein, wherein said air/fuel ratio detector and said ceramic substrate are joined to each other in layered form, wherein part of said oxygen reference electrode is shaped in a pattern having a form extremely thinner than the remaining portion thereof, and said pattern of thinner form is directly in contact with an exhaust gas atmosphere through layer-to-layer spacing of said laminated body which constitutes said air/fuel ratio detector, and wherein said oxygen reference electrode, said negative electrode and said positive electrode in said laminated body constituting said air/fuel ratio detector are provided so as to be shorter in length than said dense solid electrolyte, said porous solid electrolyte and said protection film and biased to a longitudinally-extending one end of said laminated body, whereby said air/fuel ratio detector is positioned at a longitudinally-extending one end of a laminated structure, and a pattern for said heater is shaped in the form of such a pattern that said air/fuel ratio detector side is dense and gradually becomes less dense towards an end on the opposite side of said air/fuel ratio detector as viewed in the longitudinal direction of said laminated body.

2. The air/fuel ratio sensor according to claim 1, wherein said oxygen reference electrode, said negative electrode and said positive electrode are respectively composed of a porous electrode material comprised of a platinum base material, said heater is composed of a platinum base material, and wherein said ceramic substrate is composed of alumina.

3. The air/fuel ratio sensor according to claim 1, wherein one or more thermal stress buffer layers each having an intermediate thermal expansion coefficient between said dense solid electrolyte and said ceramic substrate are interposed between said dense solid electrolyte of said air/fuel ratio detector and said ceramic substrate having said heater built therein.

4. The air/fuel ratio sensor according to claim 3, wherein said dense solid electrolyte is zirconia, said ceramic substrate is alumina, and said thermal stress buffer layers are respectively composed of a mixed material of zirconia and alumina.

5. The air/fuel ratio sensor according to claim 1, wherein at least one of an HC detector and an NOx detector comprised of an oxide semiconductor is provided at a surface of said ceramic substrate.

6. The air/fuel ratio sensor according to claim 5, wherein said surface of said ceramic substrate on which said HC detector or said NOx detector comprised of said oxide semiconductor is provided is opposite to a surface on which the air/fuel ratio detector is located.

7. The air/fuel ratio sensor according to claim 5, wherein the pattern for said heater built in said ceramic substrate is set so that one end side of said ceramic substrate, extending in the longitudinal direction thereof, the center thereof and the other end side thereof respectively produce temperature distributions which yield a high temperature, a middle temperature and a low temperature, and said HC detector or said NOx detector is placed in a longitudinal-extending central portion of said ceramic substrate.

8. A combined air/fuel ratio sensor, comprising:

an air/fuel ratio detector formed by stacking an oxygen reference electrode, a dense solid electrolyte, a negative electrode, a porous solid electrolyte, a positive electrode and a porous protection film on one another;

an NOx detector formed by stacking a porous oxide, an NOx detecting electrode and a dense solid electrolyte on one another; and a ceramic substrate having a heater built therein; and wherein said air/fuel ratio detector, said NOx detector and said ceramic substrate are integrally joined to one another so as to be constructed as a single laminated structure.

9. A combined air/fuel ratio sensor, comprising:

an air/fuel ratio detector formed by stacking an oxygen reference electrode, a dense solid electrolyte, a negative electrode, a porous solid electrolyte, a positive electrode and a porous protection film on one another;

an HC detector formed by stacking a porous oxide, an HC detecting electrode and a dense solid electrolyte on one another; and a ceramic substrate having a heater built therein; and wherein said air/fuel ratio detector, said HC detector and said ceramic substrate are integrally joined to one another so as to be constructed as a single laminated structure.

10. A combined air/fuel ratio sensor, comprising:

an air/fuel ratio detector obtained by stacking an oxygen reference electrode, a dense solid electrolyte, a negative electrode, a porous solid electrolyte, a positive electrode and a porous protection film on one another, said air/fuel ratio detector being formed over one surface of a ceramic substrate having a heater built therein; and an NOx detector obtained by stacking an oxygen reference electrode, a dense solid electrolyte, an NOx detecting electrode and a porous oxide on one another, said NOx detector being formed over the other surface of said ceramic substrate; and wherein the oxygen reference electrode of said air/fuel ratio detector and the oxygen reference electrode of said NOx detector are in communication with each other via a through hole defined in said ceramic substrate.

11. A combined air/fuel ratio sensor, comprising:

an air/fuel ratio detector obtained by stacking an oxygen reference electrode, a dense solid electrolyte, a negative electrode, a porous solid electrolyte, a positive electrode and a porous protection film on one another, said air/fuel ratio detector being formed over one surface of a ceramic substrate having a heater built therein; and an HC detector obtained by stacking an oxygen reference electrode, a dense solid electrolyte, an HC detecting electrode and a porous oxide on one another, said HC detector being formed over the other surface of said ceramic substrate; and wherein the oxygen reference electrode of said air/fuel ratio detector and the oxygen reference electrode of said HC detector are in communication with each other via a through hole defined in said ceramic substrate.

12. A combined air/fuel ratio sensor, comprising:

an air/fuel ratio detector formed of a laminated body obtained by stacking an oxygen reference electrode, a dense solid electrolyte, a negative electrode, a porous solid electrolyte, a positive electrode and a porous protection film on one another;

a ceramic substrate having a heater built therein, which is joined to said air/fuel ratio detector in layered form; and an NOx detector constructed by cutting out part of said porous solid electrolyte, placing a dense solid electrolyte and surrounding insulating materials in a cut-out portion formed by cutting out the part of said porous solid electrolyte, and forming an electrode over the upper surface of the placed dense solid electrolyte.

* * * * *